(12) United States Patent
Du (10) Patent No.: US 11,219,739 B2
(45) Date of Patent: Jan. 11, 2022

(54) MASSAGE GUN ATMOSPHERE LAMP (71) Applicant: Shanghai Sintang Industrial Co.,Ltd., Shanghai (CN)

(72) Inventor: Chuankui Du, Shanghai (CN)

(73) Assignee: SHANGHAI SINTANG INDUSTRIAL CO., LTD., Shanghai (CN)

( * ) Notice: Subject to any disclaimer, the term of this patent is extended or adjusted under 35 U.S.C. 154(b) by 38 days.

(21) Appl. No.: 16/909,377

(22) Filed: Jun. 23, 2020

(65) Prior Publication Data
US 2021/0361906 A1 Nov. 25, 2021

(30) Foreign Application Priority Data
May 25, 2020 (CN) .......................... 202020888156.9

(51) Int. Cl.
*A61M 21/02* (2006.01)
*F21V 23/00* (2015.01)
*F21V 23/02* (2006.01)
*F21V 23/04* (2006.01)
*A61H 7/00* (2006.01)
(Continued)

(52) U.S. Cl.
CPC ............. *A61M 21/02* (2013.01); *A61H 7/005* (2013.01); *F21S 10/02* (2013.01); *F21V 23/003* (2013.01); *F21V 23/02* (2013.01); *F21V 23/0464* (2013.01); *F21V 23/0471* (2013.01); *A61H 2201/10* (2013.01); *A61H 2201/1215* (2013.01); *A61H 2201/1671* (2013.01); *A61M 2021/0044* (2013.01); *F21V 3/00* (2013.01); *F21V 23/0421* (2013.01); *F21V 33/0004* (2013.01);
(Continued)

(58) Field of Classification Search
CPC .......... A61M 21/02; A61M 2021/0044; A61H 7/005; A61H 2201/10; A61H 2201/1215; A61H 2201/1671; F21V 23/003; F21V 23/004; F21V 23/02; F21V 23/0464; F21V 23/0471; F21V 23/04; F21V 23/0414; F21V 23/0421; F21V 33/0004; F21V 33/0064; F21V 33/0068; F21V 33/008; F21Y 2113/17; F21W 2131/20; F21S 10/02
See application file for complete search history.

(56) References Cited

U.S. PATENT DOCUMENTS

| 6,283,609 | B1 * | 9/2001 | Parsons .................. F21L 15/06 |
| | | | 362/187 |
| 10,314,762 | B1 * | 6/2019 | Marton ................ A61H 23/006 |

(Continued)

*Primary Examiner* — Alan B Cariaso
(74) *Attorney, Agent, or Firm* — Muncy, Geissler, Olds and Lowe, P.C.

(57) ABSTRACT

The present disclosure provides a novel massage gun atmosphere lamp. The massage gun atmosphere lamp includes a switch control unit, a PCB lamp control board, a sensing device, and a battery. The switch control unit is embedded onto a PCB main control board. The PCB main control board is assembled in a massage gun cavity. The PCB lamp control board is in cooperation with a lamp source, a motor, and a light-transmissive plate respectively. The sensing device is arranged in a massage gun cavity. The battery and the motor are mounted in the massage gun cavity. The PCB main control board is configured to send a level signal to the motor for rotation speed adjustment and to the PCB lamp control board for color adjustment. The lamp is convenient to use, and features high technology and smart sensing.

5 Claims, 8 Drawing Sheets

(51) Int. Cl.
  *F21S 10/02* (2006.01)
  *F21W 131/20* (2006.01)
  *F21V 3/00* (2015.01)
  *A61M 21/00* (2006.01)
  *F21Y 113/17* (2016.01)
  *F21V 33/00* (2006.01)

(52) U.S. Cl.
  CPC ...... *F21V 33/0064* (2013.01); *F21W 2131/20* (2013.01); *F21Y 2113/17* (2016.08)

(56) References Cited

U.S. PATENT DOCUMENTS

| | | | | |
|---|---|---|---|---|
| 2008/0262394 | A1* | 10/2008 | Pryor | A61N 5/0613 601/15 |
| 2012/0179077 | A1* | 7/2012 | Tuck | A61H 19/44 601/46 |
| 2014/0202493 | A1* | 7/2014 | Zelickson | A61B 17/32 134/6 |
| 2015/0112411 | A1* | 4/2015 | Beckman | A61N 5/0616 607/90 |
| 2020/0315907 | A1* | 10/2020 | Dijkstra | A61H 1/00 |

* cited by examiner

MASSAGE GUN ATMOSPHERE LAMP

TECHNICAL FIELD

The present disclosure relates to the technical field of massage gun, and in particular, relates to a novel vibration massage device atmosphere lamp.

BACKGROUND

Facing the fast rhythms in life, people are suffering a lot of pressure in personal undertakings and emotions. With constant improvement of health care awareness, people need to be adaptive to the fast rhythms in life, but also need to be relieved from various pressure. Accordingly, electric massage guns are becoming popular. Conventional massage guns usually have the characteristics of vibration speed adjustment, force or pressure sensing device, power balance indication, interchangeable massage head attachments, respectively. Currently, a large amount of types or models of massage gun products are available in the market, with various sizes, shapes, and colors.

The present disclosure is intended to provide a group of atmosphere lamps which are mounted on a head region of the conventional massage guns, to improve a sense of technology of the product, and create a good and enjoyable atmosphere for massage. During massage in a dark environment, the atmosphere lamp also achieves an illumination effect. In addition, the atmosphere lamp also emits infrared rays to achieve a therapy effect. The atmosphere lamp employs a three-color light source, which may be defined to any or multiple colors by a PCB program or by a user, and the luminance of the lamp is adjustable. The light effect can be constantly on, or blinking. A sensing device is mounted at the head of the massage gun to sense the state of the massage gun, which implements a standby state of the device. When the user turns on or starts the massage gun, different display effects are exhibited in terms of luminance, color, and frequency of the lamp. With the sensing device mounted on the head of the massage gun, the massage gun can interact with the user, or when another massage gun with this function is in contact with or in the proximity of the device, the massage gun can interact with the contacted or proximal massage gun in terms of luminance, frequency, and color. By application of the technical solution according to the present disclosure, with the massage gun, the users who is operating the massage gun may experience smartness, more interest, fashion, and beauty. In this way, the atmosphere lamp helps the massage gun devices to create more satisfaction and sense of enjoyment to the users. Therefore, a novel massage gun atmosphere lamp is introduced and provided.

SUMMARY

The present disclosure is intended to provide a novel massage gun atmosphere lamp. This atmosphere lamp creates a sense of enjoyment for massage, and achieves the effects of illumination and physical therapy. In addition, the luminance of the lamp can be adjusted. With the massage gun atmosphere lamp, the users who is operating the massage gun may experience smartness, more fun, fashion, and beauty. In this way, the atmosphere lamp helps the massage gun products to create more satisfaction and sense of enjoyment to the users.

To achieve the above object, the present disclosure provides the following technical solution: a novel massage gun atmosphere lamp, including a switch control unit, a PCB lamp control board, a sensing device, and battery; whereby the switch control unit is embedded onto a PCB main control board and configured to control power-on and power-off of an entire circuit, the PCB main control board is assembled in a massage gun cavity and connected to the PCB lamp control board, the battery, and a motor respectively via a line. A control program is further written into the PCB main control board, and the PCB main control board is configured to change color conversion of a lamp source and a rotation speed variation of the motor according to the built-in control program;

the PCB lamp control board is in cooperation with the lamp source, the motor, and a light-transmissive plate respectively and arranged in the massage gun head, the sensing device is arranged in the massage gun cavity, and the sensing device is configured to receive an external signal and transmit the received signal to the PCB main control board; and the battery is mounted in the massage gun cavity, the motor is also mounted in the massage gun cavity and connected to the PCB main control board and the battery via the line, the PCB main control board is configured to send a level signal to the motor for rotation speed adjustment and to the PCB lamp control board for color adjustment, and the lamp source is in cooperation with the PCB lamp control board for use.

Preferably, the PCB lamp control board, the light-transmissive plate, and the lamp source cooperatively define a light-emitting portion, wherein the light-emitting portion is mounted at a front position of the device proximal to a massage head attachment.

The sensing device is configured to perceive a motion state of the massage gun and issues an instruction for adjusting luminance, color temperature, and frequency via the PCB main control board; and the sensing device is further configured to perceive a light intensity of an application environment and adjust luminance or color of the atmosphere lamp.

Preferably, the light-emitting portion is configured to be turned on or turn off synchronously with the massage gun, and the PCB main control board is configured to transmit an instruction signal synchronously to the battery, the motor, and the PCB lamp control board to turn on or turn off the battery, the motor, and the PCB lamp control board.

Preferably, when the individual light-emitting portions approach to each other, two light-emitting portions interactively blink and interact with each other by color variations. When one sensing device receives a signal from another sensing device, the sensing device is configured to send the signal to the PCB main control board so that the PCB main control board issues an instruction signal to the PCB lamp control board to change a voltage supplied to the lamp source and a power supply frequency, controlling on or off a three-color light source and a display intensity thereof, and changing a light-emitting luminance and the color of the lamp source.

As compared with the current technology, the present disclosure achieves the following beneficial effects: the novel massage gun atmosphere lamp is easy to use, is novel, and creates more sense of technology over the conventional atmosphere lamps. In addition, the design of the lamp further implements such functions as smart sensing device, or an operator can switch to the desired light atmosphere mode during use, and the lamp can operate in a darker environment.

The massage gun atmosphere lamp may interact with the users, or when another massage gun with this function is in the proximity, the atmosphere lamp achieves an interactive effect in terms of luminance, frequency, and color. By application of the technical solution according to the present disclosure, with the massage gun atmosphere lamp, the users who is operating the massage gun may experience smartness, more interest, fashion, and beauty. In this way, the atmosphere lamp helps the massage gun devices to create more satisfaction and sense of enjoyment to the users.

In the drawings, 1 denotes a switch control unit, 2 denotes a PCB main control board, 3 denotes a PCB lamp control board, 4 denotes a light-transmissive board, 5 denotes a sensing device, 6 denotes a line, 7 denotes a battery, 8 denotes a lamp source, 9 denotes a motor, 10 denotes a massage gun head, and 11 denotes a light-emitting portion.

DETAILED DESCRIPTION

The technical solutions in the embodiments of the present disclosure are described in detail clearly and completely hereinafter with reference to the accompanying drawings for the embodiments of the present disclosure. Apparently, the described embodiments are only a part of embodiments of the present disclosure, but not all the embodiments of the present disclosure. Based on the embodiments of the present disclosure, all other embodiments derived by persons of ordinary skill in the art without any creative efforts shall fall within the protection scope of the present disclosure.

Figure 1:
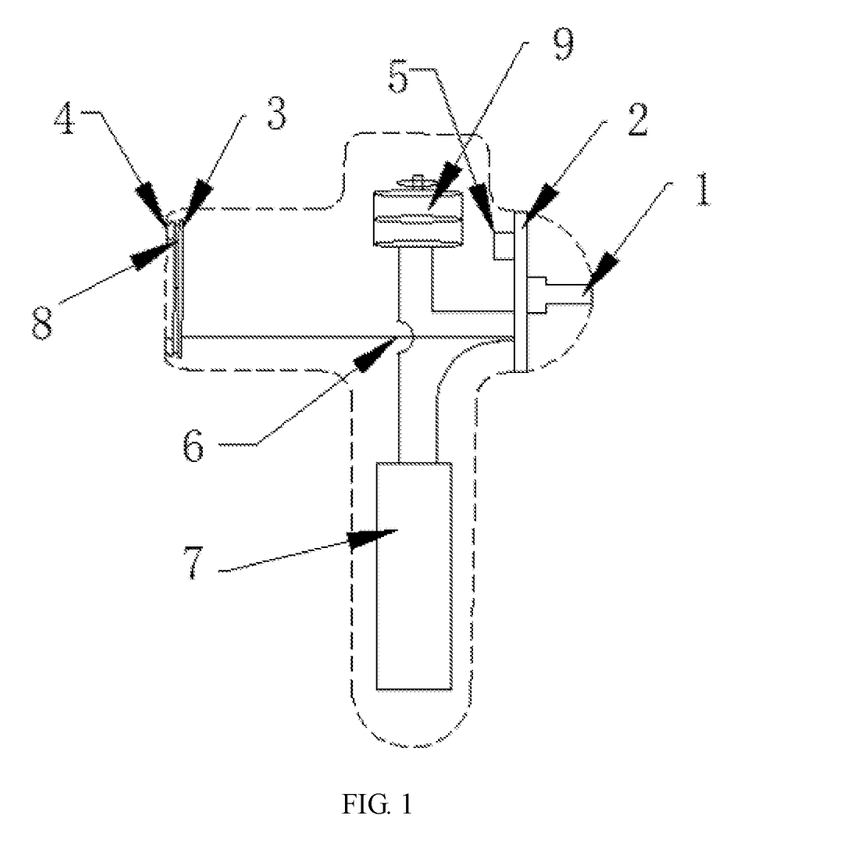
FIG. 1 is a schematic entire structural view of a massage gun atmosphere lamp according to the present disclosure.
Figure 2:
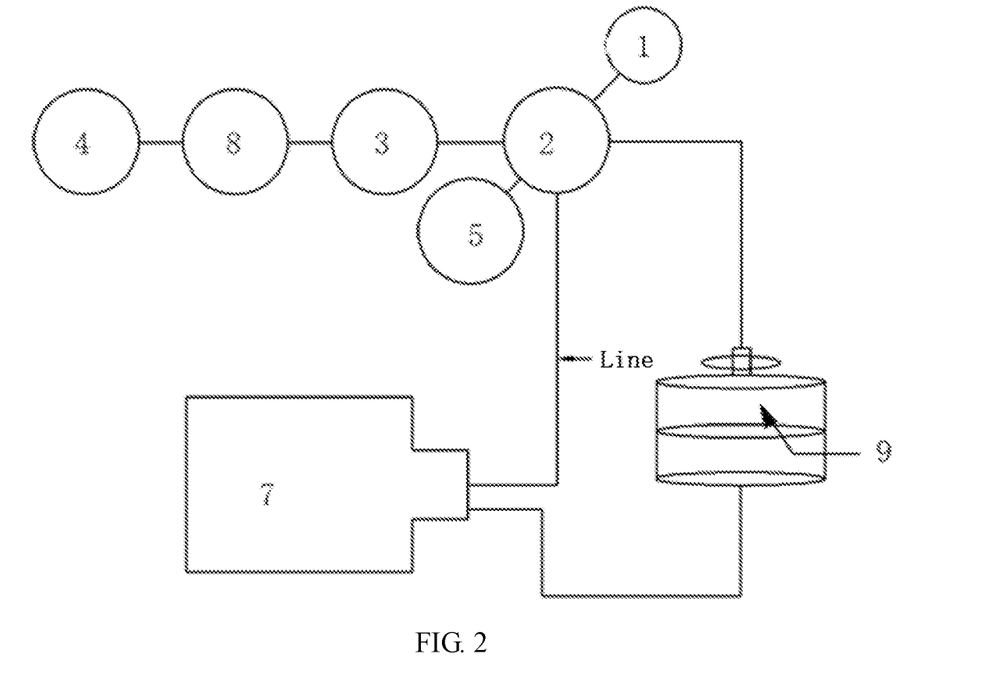
FIG. 2 is a schematic circuit structural diagram of the massage gun atmosphere lamp according to the present disclosure.

Referring to FIG. 1 to FIG. 15, the present disclosure provides a technical solution of a novel massage gun atmosphere lamp. The massage gun atmosphere gun includes a switch control unit 1, a PCB lamp control board 3, a sensing device 5, and a battery 7; wherein the switch control unit 1 is embedded onto a PCB main control board 2 and configured to control power switch of an entire circuit, the PCB main control board 2 is assembled in a massage gun cavity and connected to the PCB lamp control board 3, the battery 7, and a motor 9 respectively via a line 6, a control program is further written into the PCB main control board 2, and the PCB main control board 2 is configured to change color conversion of a lamp source 8 and a rotation speed variation of the motor 9 under control of the built-in control program;

the PCB lamp control board 3 is in cooperation with the lamp source 8, the motor 9, and a light-transmissive plate 4 respectively and arranged in a massage gun head 10, the sensing device 5 is arranged in the massage gun cavity, and the sensing device 5 is configured to receive an external signal and transmit the received signal to the PCB main control board 2; and the battery 7 is mounted in the massage gun cavity, the motor 9 is mounted in the massage gun cavity and connected to the PCB main control board 2 and the battery 7 via the line 6, the PCB main control board 2 is configured to send a level signal to the motor 9 for rotation speed adjustment and to the PCB lamp control board 3 for color adjustment, and the lamp source 9 is in cooperation with the PCB lamp control board 3 for use.

Figure 3:
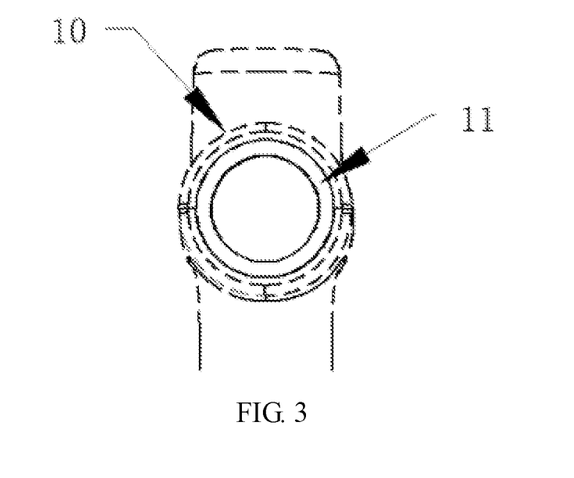
FIG. 3 is a schematic structural view of position of a light-emitting portion according to the present disclosure.
Figure 4:
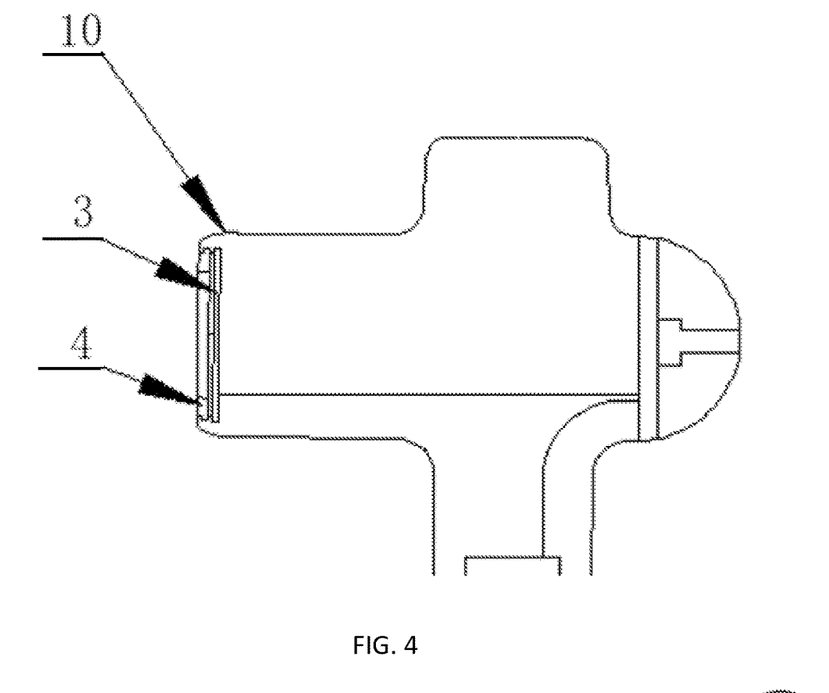
FIG. 4 is a schematic internal structural view of positions of a PCB lamp control board and a light-transmissive plate according to the present disclosure.
Figure 5:
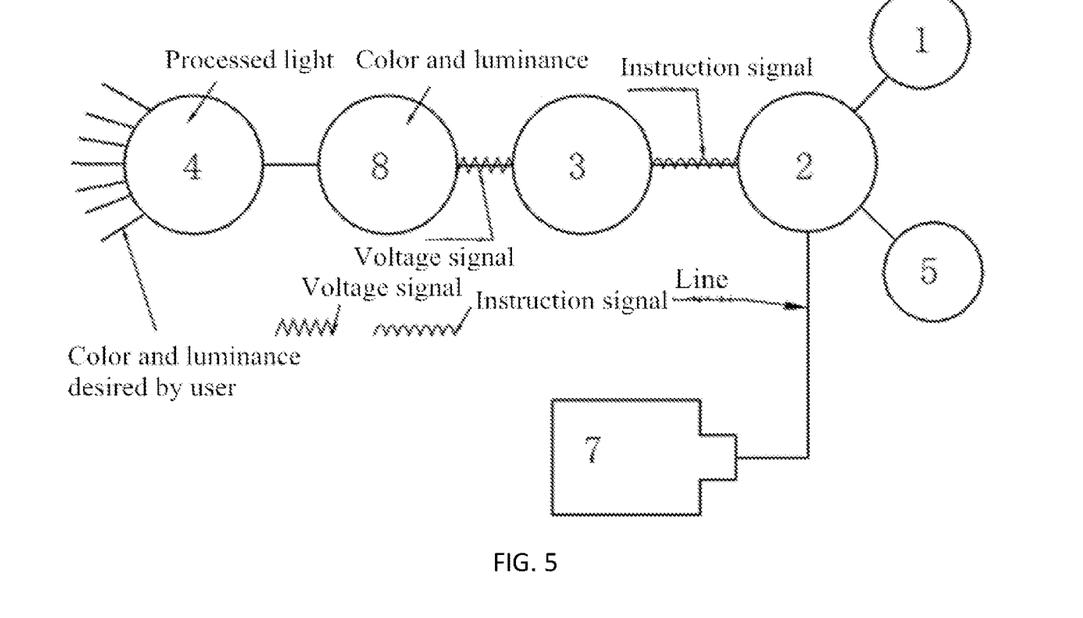
FIG. 5 is a schematic principle diagram of color and luminance adjustments according to the present disclosure.

Further, the PCB lamp control board 3, the light-transmissive plate 4, and the lamp source 8 cooperatively define a light-emitting portion 11, wherein the light-emitting portion 11 is mounted at a position of the massage gun head 10 proximal to a massage head attachment. In this way, a sense of technology may be enhanced. Referring to FIG. 4 and FIG. 5, according to the technical solution of the present disclosure, it is not limited that the atmosphere lamp is mounted at a specific position on a specific massage gun; and further, no limitation is placed onto specific use of a three-color light source, a mono-color light source, or any other types of light sources, or onto a relationship between a blink frequency, a color and a luminance of the lamp source 8.

It can be defined to emit a mono-color light, a multi-color light, or a gradually-varying light to accommodate requirements of users for selection of multiple colors. For example, when the user triggers the switch control unit 1 to adjust the rotation speed of the motor 9, if the user presses the switch control unit 1 for one time, the light may change to blue; and if the user presses the switch control unit 1 for two times, the light may change to red. The operating principles are as follows: when the user desires to adjust the color, the user may send a signal by the switch control unit 1 to the PCB main control board 2, and the PCB main control board 2 issues an instruction signal via the line 6 to the PCB lamp control board 3 to change a voltage supplied to the lamp source 8 and a power supply frequency thereof, control on or off the three-color light source and a display intensity thereof, and change the color of the lamp source 8. According to the technical solution of the present disclosure, no limitation is placed onto specific use of a three-color light source, a mono-color light source, or any other types of light sources, or onto a relationship between the blink frequency, the color and the luminance of the lamp source 8. Further, it is not limited that the atmosphere lamp is mounted on a specific massage gun.

Figure 6:
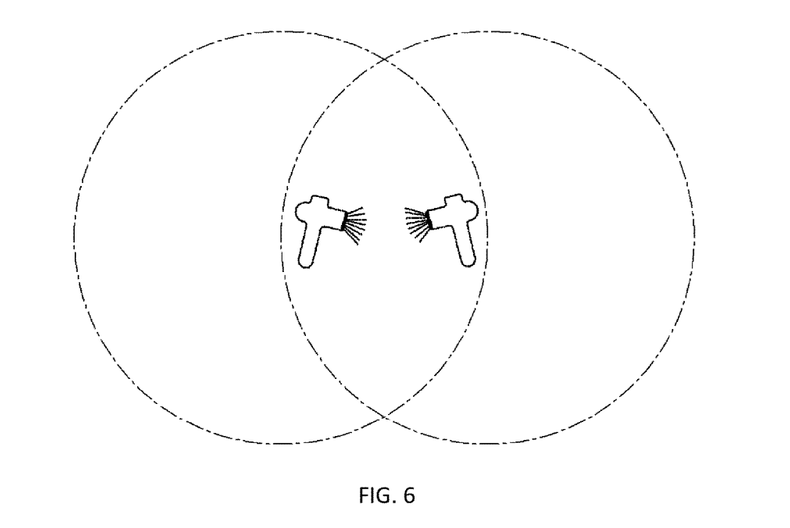
FIG. 6 is a schematic view of a sensing device according to the present disclosure.
Figure 7:
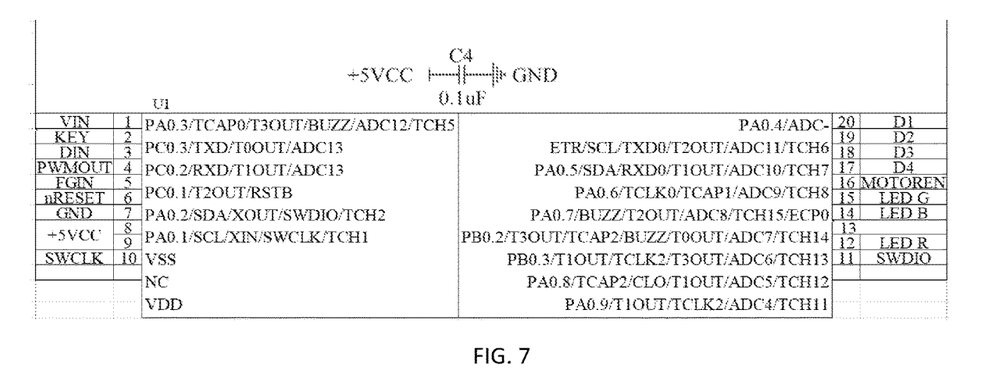
FIG. 7 is a schematic structural diagram 1 of circuit control according to the present disclosure.
Figure 8:
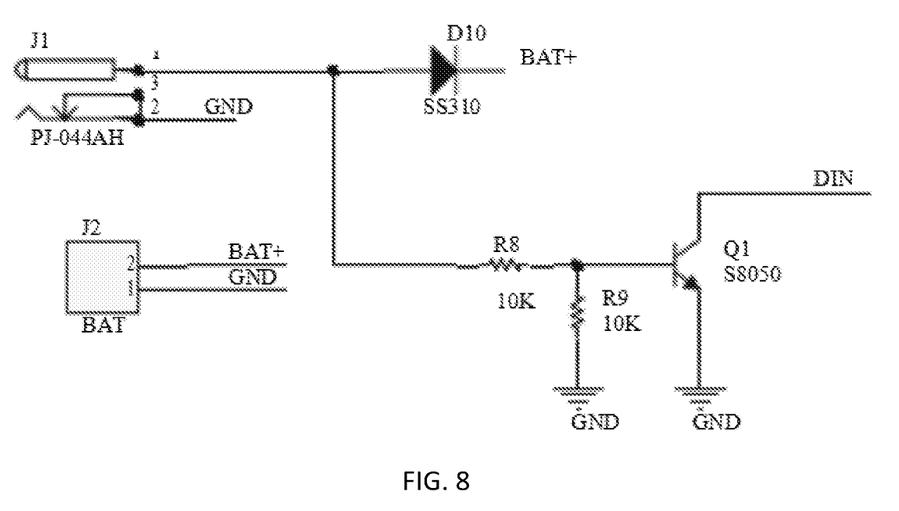
FIG. 8 is a schematic structural diagram 2 of circuit control according to the present disclosure.
Figure 9:
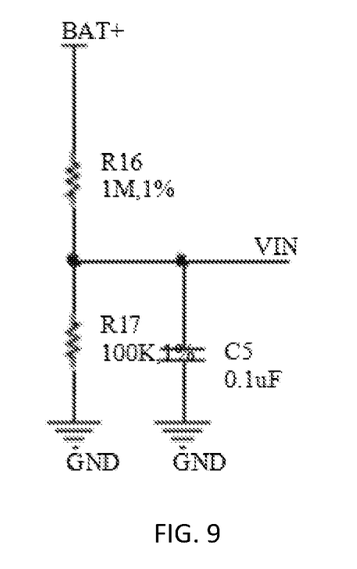
FIG. 9 is a schematic structural diagram 3 of circuit control according to the present disclosure.
Figure 10:
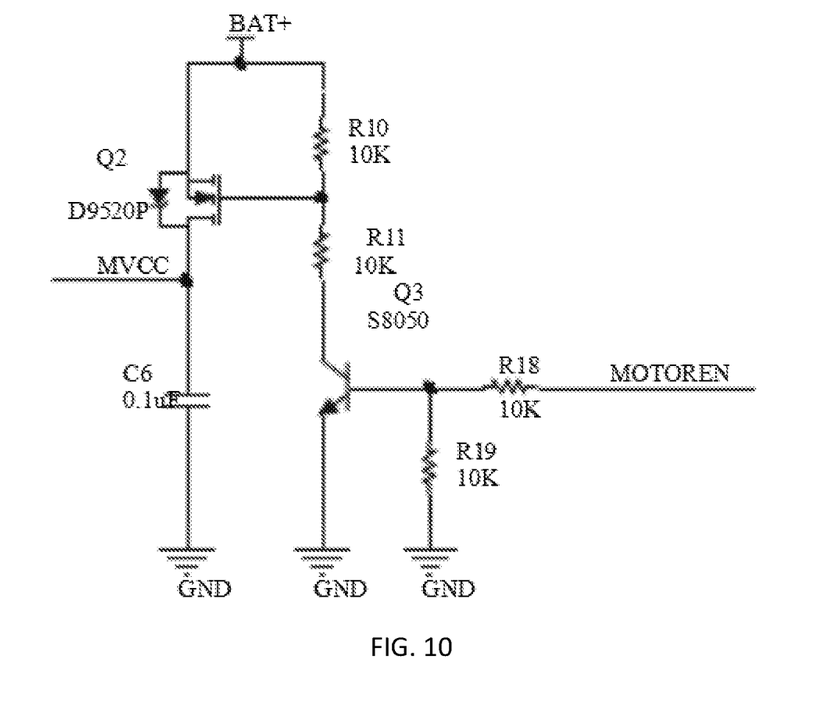
FIG. 10 is a schematic structural diagram 4 of circuit control according to the present disclosure.
Figure 11:
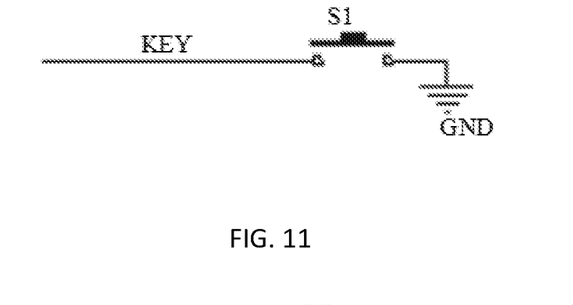
FIG. 11 is a schematic structural diagram 5 of circuit control according to the present disclosure.
Figure 12:
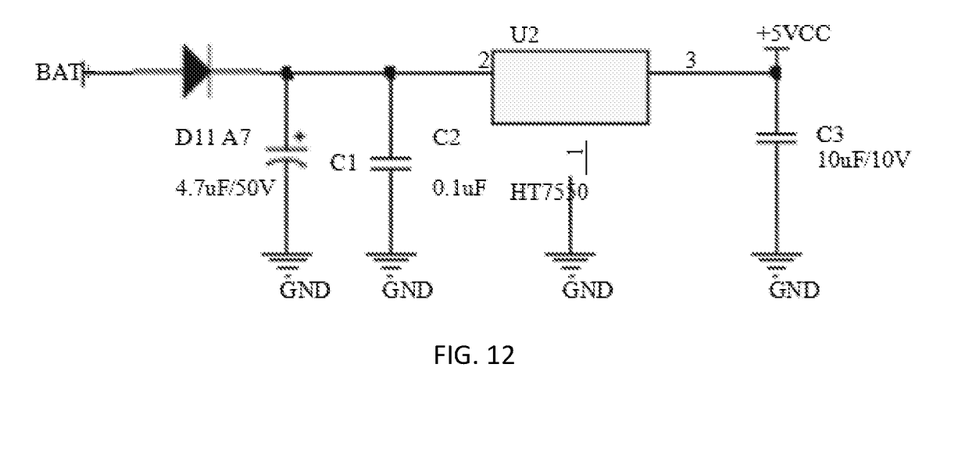
FIG. 12 is a schematic structural diagram 6 of circuit control according to the present disclosure.
Figure 13:
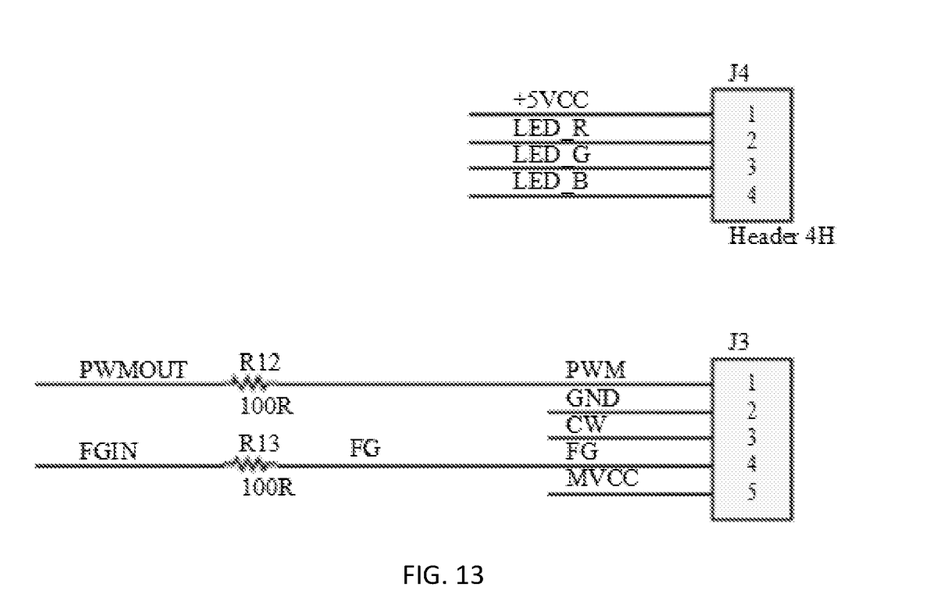
FIG. 13 is a schematic structural diagram 7 of circuit control according to the present disclosure.
Figure 14:
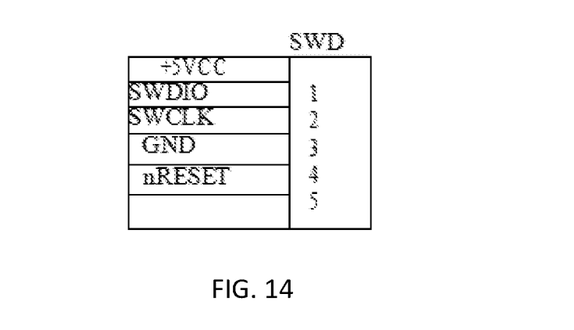
FIG. 14 is a schematic structural diagram 8 of circuit control according to the present disclosure.
Figure 15:
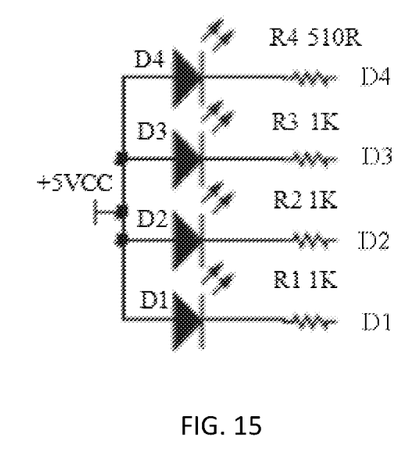
FIG. 15 is a schematic structural diagram 9 of circuit control according to the present disclosure.

Further, the sensing device 5 is configured to perceive a motion state of the massage gun and issues an instruction for adjusting luminance, color, and frequency via the PCB main control board 2; and the sensing device 5 is further configured to perceive a light intensity of an application environment and adjust luminance or color of the atmosphere lamp.

When the massage gun is in a stationary state, the light can be dimmed to save power; and when the massage gun is held by a user on the hands or in a motion state, the luminance of the light may be increased. The operating principles are as follows: when the sensing device 5 senses that the massage gun is in the stationary state or the motion state that is varying, the sensing device 5 feeds back a signal to the PCB main control board 2, and the PCB main control board 2 issues an instruction signal via the line 6 to the PCB lamp control board 3 to change a current supplied to the lamp source 8 and a power supply frequency thereof, control on or off the three-color light source and the display intensity thereof, and change the color, the luminance, and the blink frequency of the lamp source 8. According to the technical solution of the present disclosure, no limitation is placed onto specific use of a light sensing device, a sound sensing device, a sensing device of mercury sensing or other types, onto a position where the sensing device 5 is mounted, or onto specific use a three-color light source, a mono-color light source, or other types of light sources. In addition, no limitation is placed onto variations of the motion and stationary states of the massage gun, or onto a relationship between the blink frequency, the color, and the luminance of the lamp source 8. Further, it is not limited that the atmosphere lamp is mounted on a specific massage gun.

In addition, the light intensity of the massage gun can be automatically adjusted as the light in the ambient environment varies. When the light in the ambient environment is sufficient, the display luminance of the atmosphere lamp is lowered; and when the light in the ambient environment is insufficient, the display luminance of the atmosphere lamp is increased. The operating principles are as follows: when the sensing device 5 senses that the light intensity in the ambient environment varies, the sensing device 5 feeds back a signal to the PCB main control board 2, and the PCB main control board 2 issues an instruction signal via the line 6 to the PCB lamp control board 3 to change a current supplied to the lamp source 8 and a power supply frequency thereof, control on or off the three-color light source and the display intensity thereof, and change the color and the luminance of the lamp source 8. According to the technical solution of the present disclosure, no limitation is placed onto specific use of a three-color light source, a mono-color light source, or any other types of light sources, or onto light intensity variations in the ambient environment, or onto a relationship between the blink frequency, the color and the luminance of the lamp source 8. Further, it is not limited that the atmosphere lamp is mounted on a specific massage gun.

Preferably, the light-emitting portion 11 is configured to be turned on or turn off synchronously with the massage gun, and the PCB main control board 2 is configured to transmit an instruction signal synchronously to the battery 7, the motor 9, and the PCB lamp control board 3 to turn on or turn off the battery 7, the motor 9, and the PCB lamp control board 3; when the massage gun is turned on, the light is synchronously turned on; when the massage gun is turned off, the light is synchronously turned off; and when the massage gun enters a standby state, the light blinks slowly. The operating principles are as follows: when the operating and power supplying states of the massage gun change, the PCB main control board 2 issues an instruction signal via the line 6 to the battery 7, the motor 9, and the PCB lamp control board 3 concurrently such that the battery 7, the motor 9, and the PCB lamp control board 3 are synchronously turned on or turned off. According to the technical solution of the present disclosure, no limitation is placed onto a relationship between the blink frequency, the color, and the luminance of the lamp source 8 when the lamp source 8 is turned on, enters the standby state, and turned off, or onto specific use of a three-color light source, a mono-color light source, or any other types of light sources. Further, it is not limited that the atmosphere lamp is mounted on a specific massage gun.

Further, when the individual light-emitting portions 11 approach to each other, two light-emitting portions 11 interactively blink and interact with each other by color variations. That is, when one sensing device 5 receives a signal from another sensing device 5, the sensing device 5 may send the signal to the PCB main control board 2 so that the PCB main control board 2 issues an instruction signal to the PCB lamp control board 3 to change the voltage supplied to the lamp source and the power supply frequency, control on or off the three-color light source and the display intensity thereof, and change the light-emitting luminance and the color of the lamp source. When in two massage guns with this function, if a sensing device 5 in one massage gun perceives a signal at a specific frequency from a sensing device 5 in the other massage gun, the atmosphere lamp may exhibit luminance and color variations, or blink at a specific frequency, as illustrated in FIG. 6. The operating principles are as follows: when the sensing device 5 of one massage gun receives a signal from the sensing device 5 in another massage gun, the signal may be sent to the PCB main control board 2 such that the PCB main control board 2 issues an instruction signal via the line 6 to the PCB lamp control board to change the voltage supplied to the lamp source 8 and the power supply frequency thereof, and control on or off of the three-color light source and the display intensity thereof, and change the color and the luminance of the lamp source 8. According to the technical solution of the present disclosure, no limitation is placed onto specific use of a three-color light source, a mono-color light source, or any other types of light sources, onto a relationship between the specific blink frequency, the color, and the luminance of the lamp source 8, or onto specific use of a light sensing device, a sound sensing device, a signal sensing device, or any other types of sensing device 5. Further, it is not limited that the atmosphere lamp is mounted on a specific massage gun.

In the meantime, the massage gun atmosphere lamp can be deployed in a music environment, and the light can be rhythmic with music. For example, the quicker the rhythm of the music, the quicker the lamp blinks; and the slower the rhythm of the music, the slower the lamp blinks. The operating principles are as follows: when the sensing device 5 receives an external music signal, the sensing device 5 sends the signal to the PCB main control board 2, and the PCB main control board 2 issues an instruction signal via the line 6 to the PCB lamp control board 3 to change the voltage supplied to the lamp source 8 and the power supply frequency thereof, and controls on or off the three-color light source and the display intensity thereof, and change the color and the luminance of the lamp source 8 respectively. According to the technical solution of the present disclosure, no limitation is placed onto specific use of a three-color light source, a mono-color light source, or any other types of light sources, onto a relationship between a blink frequency, a color and a luminance of the lamp source 8, or onto specific use of a light sensing device, a sound sensing device, a signal sensing device, or any other types of sensing devices 5. Further, it is not limited that the atmosphere lamp is mounted at a specific position on a specific massage gun. In addition, the user may define and select a plurality of light projection scenario modes, for example, a star pattern scenario, a sea pattern scenario, a forest pattern scenario, and more. The operating principles are as follows: when the user desires to adjust the light scenario mode, the user may send a signal by the switch control unit 1 to the PCB main control board 2, and the PCB main control board 2 issues an instruction signal via the line 6 to the PCB lamp control board 3 so that the PCB lamp control board controls variations of the lamp source 8. Afterwards, the lamp source 8 projects a pattern scenario by the light-transmissive plate 4, for example, if the switch control unit 1 is pressed for 2 seconds, the pattern scenario can be changed. According to the technical solution of the present disclosure, no limitation is placed onto specific time for pressing the switch control unit 1, or onto a relationship between a displayed pattern scenario, the blink frequency, the color, and the luminance. Further, it is not limited that the atmosphere lamp is mounted on a specific massage gun.

In addition, the infrared lamp source 8 may be additionally provided with a heating function. For example, during use of the massage gun for massage, infrared heating is employed for infrared physical therapy, which helps to activate blood, improve blood circulation, and enhance metabolism, quicken circulation of blood and lymphatic systems, which promotes absorption and elimination of abnormal tissues, and improve the immunity of the body system. The operating principles are as follows: the user can send a signal by the switch control unit 1 to the PCB main control board 2 such that the PCB main control board 2 issues an instruction signal to the PCB lamp control board 3, and the PCB lamp control board 3 changes the voltage supplied to the lamp source 8, the power supply frequency thereof, and the light-emitting heat of the lamp source 8. In this away, electromagnetic waves of the infrared rays are controlled, the infrared rays irradiate the outside through the light-transmissive plate 4, thereby achieving the effect of physical therapy by infrared heating. According to the technical solution of the present disclosure, no limitation is placed onto specific use of a near-infrared lamp source 8, a medium infrared lamp source 8, any other types of lamp sources 8, or onto a relationship between the blink frequency, the color and the luminance of the infrared lamp source 8. Further, it is not limited that the atmosphere lamp is mounted on a specific massage gun.

The standard parts involved in the present application can all be purchased from the market, and the specially-shaped parts can be customized according to the description and the drawings. The connection method between all the parts is currently conventional method used in the current technology, such as screen and bolt connection, rivet connection, welding, etc. The machines, parts and devices are all conventional models used in the current technology. The circuit connections employ the conventional connection modes in the current technology. Details about these are not described herein any further.

Described above are exemplary embodiments of the present invention, which are not intended to limit the protection scope of the present invention. Although the present invention is described in detail with reference to the above embodiments, a professional person in the field would still make modifications to the technical solution disclosed in the specific embodiments, or would still make equivalent replacements to a part of the technical features therein. These modifications, equivalent replacements, improvements, etc. shall be considered as falling within the protection scope of the present disclosure.

What is claimed is:

1. A novel massage gun atmosphere lamp, comprising a switch control unit (1), a PCB lamp control board (3), a sensing device (5), and a battery (7); wherein the switch control unit (1) is embedded onto a PCB main control board (2) and configured to control power-on and power-off of an entire circuit, the PCB main control board (2) is assembled in a massage gun cavity and connected to the PCB lamp control board (3), the battery (7), and a motor (9) respectively via a line (6), a control program is further written into the PCB main control board (2), and the PCB main control board (2) is configured to change color conversion of a lamp source (8) and a rotation speed variation of the motor (9) under control of the built-in control program;

the PCB lamp control board (3) is in cooperation with the lamp source (8), the motor (9), and a light-transmissive plate (4) respectively and arranged in a massage gun head (10), the sensing device (5) is arranged in the massage gun cavity, and the sensing device (5) is configured to receive an external signal and transmit the received signal to the PCB main control board (2);

and the battery (7) is mounted in the massage gun cavity, the motor (9) is mounted in the massage gun cavity and connected to the PCB main control board (2) and the battery (7) via the line (6), the PCB main control board (2) is configured to send a level signal to the motor (9) for rotation speed adjustment and to the PCB lamp control board (3) for color adjustment, and the lamp source (9) is in cooperation with the PCB lamp control board (3) for use.

2. The novel massage gun atmosphere lamp according to claim 1, wherein the PCB lamp control board (3), the light-transmissive plate (4), and the lamp source (8) cooperatively define a light-emitting portion (11), wherein the light-emitting portion (11) is mounted at a position of the massage gun head (10) proximal to a massage head.

3. The novel massage gun atmosphere lamp according to claim 1, wherein the sensing device (5) is configured to perceive a motion state of the massage gun and issues an instruction for adjusting luminance, color temperature, and frequency via the PCB main control board (2); and the sensing device (5) is further configured to perceive a light intensity of an application environment and adjust luminance or color of the atmosphere lamp.

4. The novel massage gun atmosphere lamp according to claim 2, wherein the light-emitting portion (11) is configured to be turned on or turn off synchronously with the massage gun, and the PCB main control board (2) is configured to transmit an instruction signal synchronously to the battery (7), the motor (9), and the PCB lamp control board (3) to turn on or turn off the battery (7), the motor (9), and the PCB lamp control board (3).

5. The novel massage gun atmosphere lamp according to claim 2, wherein when the individual light-emitting portions (11) approach to each other, two light-emitting portions (11) interactively blink and interact with each other by color variations; wherein when one sensing device (5) receives a signal from another sensing device (5), the sensing device is configured to send the signal to the PCB main control board (2) such that the PCB main control board (2) issues an instruction signal to the PCB lamp control board (3) to change a voltage supplied to the lamp source (8) and a power supply frequency, control on or off a three-color light source and a display intensity thereof, and change a light-emitting luminance and the color of the lamp source (8).

* * * * *